(12) United States Patent
Lax et al.

(10) Patent No.: US 8,932,651 B2
(45) Date of Patent: Jan. 13, 2015

(54) FUNCTIONAL FOOD PRODUCT COMPRISING HEAT SHOCK PROTEIN OR A HYDROLYSATE THEREOF

(75) Inventors: Julia Lax, Brüggen (DE); Federico G. Seifarth, Westlake, OH (US)

(73) Assignee: Alfa Biogene International B.V. (DE)

( * ) Notice: Subject to any disclaimer, the term of this patent is extended or adjusted under 35 U.S.C. 154(b) by 268 days.

(21) Appl. No.: 13/193,825

(22) Filed: Jul. 29, 2011

(65) Prior Publication Data

US 2012/0021971 A1 Jan. 26, 2012

Related U.S. Application Data

(63) Continuation of application No. PCT/EP2010/051111, filed on Jan. 29, 2010.

(30) Foreign Application Priority Data

Jan. 29, 2009 (EP) .................................... 09151656

(51) Int. Cl.
| | | |
|---|---|---|
| *A61K 36/00* | (2006.01) | |
| *A61K 38/16* | (2006.01) | |
| *A23L 1/29* | (2006.01) | |
| *A23L 1/305* | (2006.01) | |
| *C07K 14/415* | (2006.01) | |

(52) U.S. Cl.
CPC ............... *A61K 38/168* (2013.01); *A23L 1/296* (2013.01); *A23L 1/3053* (2013.01); *A23L 1/3055* (2013.01); *C07K 14/415* (2013.01)
USPC ........... 424/725; 514/1.1; 514/16.6; 514/16.8

(58) Field of Classification Search
None
See application file for complete search history.

(56) References Cited

U.S. PATENT DOCUMENTS

| | | | |
|---|---|---|---|
| 6,007,821 A * | 12/1999 | Srivastava et al. | ......... 424/193.1 |
| 6,312,711 B1 | 11/2001 | Duchateau et al. | |
| 2002/0006410 A1 | 1/2002 | Lukacs et al. | |
| 2006/0089302 A1* | 4/2006 | Abulafia-Lapid et al. | ...... 514/12 |

FOREIGN PATENT DOCUMENTS

| | | |
|---|---|---|
| EP | 1531160 A1 | 5/2005 |
| WO | 02/098910 A1 | 12/2002 |

OTHER PUBLICATIONS

Wieten, et al., "IL-10 is Critically Involved in Mycobacterial HSP70 Induced Suppression of Proteoglycan-Induced Arthritis," PLoS ONE, Jan. 2009, vol. 4, Issue 1, e4186.
International Search Report relating to corresponding PCT/EP2010/051111, Jul. 20, 2010.
Author unknown, "Project HSP," Feb. 2, 2008, 1-2.
Ahn, et al., "Protective Role of Heat Shock and Heat Shock Protein 70 in Lactacystin-Induced Cell Death Both in the Rat Substantia Nigra and PC12 Cells," Brain Research, 1087 (2006) 159-167.
Evans, et al., "Heat Shock Proteins 70 and 90 Inhibit Early Stages of Amyloid β-(1-42) Aggregation in Vitro," The Journal of Biological Chemistry, vol. 281, No. 44, Nov. 3, 2006.
Pockley, A. Graham, "Heat Shock Proteins, Inflammation, and Cardiovascular Disease," Journal of the American Heart Association, 2002; 105; 1012-1017.
van Eden, et al., "Heath-Shock Proteins Induce T-Cell Regulation of Chronic Inflammation," Nature, 318, Apr. 2005, vol. 5.
Hamman, Josias H., et al.,"Oral Delivery of Peptide Drugs," Biodrugs, 2005, pp. 165-177, vol. 19, No. 3, Adis Data Information BV.
Mahato, Ram I., et al.,"Emerging Trends in Oral Delivery of Peptide and Protein Drugs," Critical Reviews in Therapeutic Drug Carrier Systems, 2003, pp. 153-214, vol. 20, No. 2&3, Begell House, Inc.
Morishita, Mariko, et al.,"Is the Oral Route Possible for Peptide and Protein Drug Delivery?," Drug Discovery Today, Oct. 2006, pp. 905-910, vo. 11, No. 19/20, Elsevier Ltd.
Soltero, Richard, et al.,"The Oral Delivery of Protein and Peptide Drugs," Innovations in Pharmaceutical Technology, Dec. 2001, pp. 106-110.

* cited by examiner

*Primary Examiner* — Susan Hoffman
(74) *Attorney, Agent, or Firm* — Banner & Witcoff, Ltd.

(57) ABSTRACT

The invention relates to a heat shock protein from alfalfa and/or a hydrolysate of a heat shock protein from alfalfa in the manufacture of a food product for the prophylactic or therapeutic treatment of a chronic inflammatory disorder. Further, the invention relates to a clinical food product comprising heat shock protein from alfalfa and/or a hydrolysate of a heat shock protein from alfalfa.

12 Claims, No Drawings

FUNCTIONAL FOOD PRODUCT COMPRISING HEAT SHOCK PROTEIN OR A HYDROLYSATE THEREOF

RELATED APPLICATION DATA

This application is a continuation of PCT application number PCT/EP2010/051111 designating the United States and filed Jan. 29, 2010; which claims the benefit of EP patent application number 09151656.7 and filed Jan. 29, 2009 both of which are hereby incorporated by reference in their entireties.

FIELD OF THE INVENTION

The invention relates to the use of a heat shock protein or hydrolysate thereof in the manufacture of a food product and to a food product comprising a heat shock protein or a hydrolysate thereof.

BACKGROUND OF THE INVENTION

Heat shock proteins (HSPs) are formed by micro-organisms, plants and animals especially when, as a result of a change in the environment such as exposure to heat, radiation or chemicals, so-called stress-susceptible genes are expressed. According to current insights, such proteins can contribute to a protection against detrimental effects resulting from such environmental changes. For that reason, the use of heat shock is in the centre of interest of, inter alia, medicine.

WO 95/25744 amongst others describes a microbial heat shock protein which may be used for protection against or treatment of an inflammatory disease.

WO 02/24220 relates to a vaccine on the base on an immunogenic mixture composed of heat stress proteins derived from fresh herbaceous plant cells with exterior antigens from pathogenic microorganisms or malformed somatic tissues/cells of Homo or their synthetic analogues or with interior antigen derived from malformed somatic tissues and/or urine, which were obtained from malformed somatic tissues and/or urine or their synthetic analogues.

WO 2008/047243 relates to a pharmaceutical composition for suppression of apoptosis comprising a fusion protein.

EP 1 531 160 A1 relates to a method for recovering a heat shock protein, in particular a plant heat shock protein. Further, it is mentioned that the plant heat shock protein may be used as a medicament.

The inventors have now realised that a specific HSP or hydrolysate thereof may be used in the manufacture of a food product for the treatment of a specific disorder.

Accordingly, the present invention is directed to the use of a heat shock protein from alfalfa or an other plant and/or a hydrolysate of a heat shock protein from alfalfa or an other plant in the manufacture of a food product for the prophylactic or therapeutic treatment of a chronic inflammatory disorder and/or an autoimmune disease.

In particular, the food product may be a clinical food product, a dairy food product or substitute thereof. Further, the invention is directed to a food product, which may in particular, be intended for administration to a subject suffering from a chronic inflammatory disorder or for use in a diet aimed at preventing the developing a chronic inflammatory disorder.

Accordingly, the invention further relates to a clinical food product comprising a heat shock protein from alfalfa or another plant and/or a hydrolysate of a heat shock protein from alfalfa or another plant.

Further the invention in particular relates to a food product comprising heat shock protein from alfalfa or another plant and/or a hydrolysate of heat shock protein from alfalfa or another plant, selected from the group of dairy products, such as yoghurt, ice-cream, other milk-based desserts, milk, yoghurt-drinks, butter; dairy-substitute products, i.e. dairy-product like products wherein milk has been replaced by an other protein-containing liquid, such as rice-milk, soy milk or the like; fruit products and soft drinks In a specific embodiment, the invention relates to a food product, comprising microparticles which microparticles comprise a heat shock protein from alfalfa or another plant and/or a hydrolysate of a heat shock protein from alfalfa or another plant and an encapsulating material, in particular an enteric encapsulating material or another acid-stable encapsulating material. Such product may in particular be a product that is for oral consumption e.g. a dairy product) or for enteral tube feeding.

Compared to a vaccine, e.g. as described in WO 02/24220 a food product according to the invention is in particular advantageous in that it can be administered as (part of) the normal diet (or as part of a normal clinical feeding procedure) and, importantly, that the food product of the invention may advantageously be free of added exterior antigens from pathogenic micro-organisms or malformed somatic tissues/cells of the subject (usually human) and synthetic analogues thereof, and free of interior antigens derived from malformed somatic tissues and/or urine and synthetic analogues thereof. It is noted that, in principle antigens may be present in the food product, in particular in a food intended to be taken orally or by tube feeding, e.g. probiotica or certain other food ingredients (e.g. specific proteins) may potentially be antigenic, and in some embodiments remains of micro-organisms (killed as a result of pasteurisation or sterilisation) may be present without being harmful to the subject. If present, such antigens may be mixed or not mixed with the HSP or HSP-hydrolysate. In case HSP or HSP-hydrolysate is present in the form of microparticles, and such antigens are present, they usually do not form part of the microparticles.

Compared to a (clinical) product comprising mammalian or microbial HSP, it is further considered that the HSP in a product according to the invention is advantageous in that specific contaminations are generally absent, that may be present in mammalian HSP or microbial HSP, e.g. pathogenic viruses or prions in the case of mammalian HSP or endotoxins in case of microbial HSP.

Besides its effectiveness in the therapeutic or prophylactic treatment of a subject suffering from or being at risk of developing a chronic inflammatory disorder it is envisaged that the HSP or HSP-hydrolysate from alfalfa or another plant is advantageous in that it is hypo-allergenic compared to e.g. microbial HSP or microbial HSP-hydrolysate.

Further, it is envisaged that in at least some embodiments the HSP or HSP hydrolysate in a product of the invention may have an anti-allergenic effect.

Further, it is contemplated that a heat shock protein from alfalfa or another plant and/or a hydrolysate of a heat shock protein from alfalfa or another plant may be used for the treatment of a septic or anaphylactic shock, in particular in a food product according to the invention.

Further, alfalfa HSP may be used therapeutically or prophylactically to help stabilize or boost the immune system.

It is in particular contemplated that a food product according to the invention may have an inducing effect on HSP-specific regulatory T-cells. Further, it is contemplated that the activated T-cells cross-recognise endogenous HSP presented by cells of tissue that is under threat of inflammation or already inflamed. It is envisaged that the administration of a food product comprising HSP or HSP-hydrolysate from alfalfa or another plant, may thus improve the immune system in that, e.g., auto-antigens may be recognised better and that thus an autoimmune related chronic inflammation, for instance atherosclerosis or arthritis, that has manifested itself can be treated or that administration of the food product can contribute to prevent the development of an autoimmune related chronic inflammation.

The term "or" as used herein is defined as "and/or" unless specified otherwise.

The term "a" or "an" as used herein is defined as "at least one" unless specified otherwise.

When referring to a moiety (e.g. a compound) in the singular, the plural is meant to be included, unless specified otherwise.

A food product as used herein refers to a nutritional product in general. For example, a food product may refer to a parenteral nutritional product that can be fed to a person intravenously. A food product may also refer to a clinical food product or an infant formula.

A chronic inflammatory disorder may be defined herein as a disorder wherein at least one of the symptoms is chronic inflammation or wherein the disorder is caused at least in part by chronic inflammation. Chronic inflammation leads to a progressive shift in the type of cells which are present at the site of inflammation and involves destruction of the tissue from the inflammatory process. Chronic inflammation should be distinguished from acute inflammation. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue.

A food product in accordance with the invention generally is a food product, comprising HSP or hydrolysate thereof that has been separated, in particular isolated from the source (the plant or part thereof) wherein it has been produced. Suitable ways to obtain the HSP are known in the art per se, for instance from EP 1 531 160 A1.

In addition to the HSP or HSP-hydrolysate the food product usually comprises at least one food component selected from the group of proteins other than HSP, in particular one or more proteins selected from dairy proteins, cereal proteins, soy proteins, egg proteins, rice proteins, nut proteins, proteins from animals; oligopeptides other than oligopeptides from HSP-hydrolysate; digestible carbohydrates (e.g. monosaccharides, disaccharides, digestible oligosaccharides, digestible polysaccharides, such as starch); dietary fibres (such as indigestible polysaccharides); amino acids; minerals; vitamins; edible fats and oils;

The term clinical food product as used herein, is used for a food product that is intended to be administered other than by normal oral ingestion (peroral administration), such as in particular by parenteral administration or via enteral feeding (e.g. tube feeding). Generally, clinical food products are liquids, e.g. the clinical food may be an emulsion, a suspension or a syrup. The clinical food product may for example be an enteral or tube feeding. Preferably, no chewing is required to suitably consume the clinical food product.

Preferably, the food product of the invention is administered via enteral administration. Enteral administration as used herein refers to the introduction of a product into the stomach or intestines, such as by tube feeding or by peroral administration (such as eating). In particular enteral administration refers to the introduction of a product into the stomach or intestines via a tube. Even more preferably, enteral administration is done by intragastric gavage, which is the introduction of a product into the stomach via a tube. Surprisingly, enterally administered alfalfa HSP, in particular alfalfa HSP introduced into the stomach via a tube, has been found to be effective in the treatment of a disease that is not a disease of the gastro-intestinal tract, such as chronic inflammatory disorder or autoimmune diseases, in particular in the treatment of chronic arthritis. Examples of intragastric gavage are gastrogavage, wherein the product is administered into the stomach through a tube through a surgically created opening, and nasogastric intubation, wherein a product is administered via plastic tube that is inserted through the nose, past the throat, and down into the stomach. Examples of suitable tubes, called feeding tubes, are gastric feeding tubes, nasogastric feeding tubes and duodenal feeding tubes.

The food product of the invention may also be administered via parenteral administration or via mucosal administration. Parenteral administration as used herein refers to the administration of a food product by means of injection, such as injection into a vein (intravenous administration), into a muscle (intramuscular administration) or under the skin (subcutaneous administration). Mucosal administration is the administration through mucosal surfaces, such as through the mucosa of the nose (intranasal administration) or through the mucosa of the mouth (oral administration).

It is contemplated that enteral feeding may offer advantages over parenteral feeding, including lower cost, greater convenience, decreased infectious complications, and enhanced host immune function. Another beneficial effect includes improved maintenance of gastro-intestinal mucosal structure and function, which could possibly prevent gut atrophy and bacterial translocation. On the other hand, in some embodiments parenteral feeding may be the choice of administration, e.g. in case the gastro-intestinal tract is not functioning or should be by-passed for medical reasons or possibly, in case it is desired that the HSP or hydrolysate should become distributed in the body relatively quickly. This may, e.g. be beneficial in case treatment with a product of the invention is (also) directed at treatment of septic or anaphylactic shock.

Preferably, the HSP is a natural, i.e. non-recombinant, HSP; the HSP-hydrolysate preferably is a hydrolysate from natural (non-recombinant) HSP. It is contemplated that a natural HSP or hydrolysate of natural HSP may be tolerated better by the subject treated with the food product, in particular that the risk of allergenic reactions may be less.

A product according to the invention may comprise native HSP or denaturated HSP.

The product according to the invention may be full length HSP, for example full length HSP70. Full length HSP as defined herein refers to HSP that has at least 90%, preferably 95%, more preferably 99% of the peptide length of the same type of HSP found in the plant from which the HSP originates. Full length HSP may still have lipid groups and/or sugar groups attached to the protein, which may affect the efficiency of HSP in the treatment of chronic inflammatory disorder.

HSP or HSP-hydrolysate from alfalfa is particularly preferred. HSP from alfalfa has a high similarity with HSP from humans, making it particularly suitable for use in the treatment of humans. For example, the peptide segments relevant for immune response in HSP70 from alfalfa shows, in contrast with HSP70 from other organisms, no differences in amino acid sequence between human HSP70, as can be seen in Table 1 and Table 2.

TABLE 1 first segment:

| | | |
|---|---|---|
| Human[1] | LNVLRIINEPTAAAIAYGLD (SEQ ID NO: 1) | # differences human SEQ |
| Alfalfa[2] | LNVLRIINEPTAAAIAYGLD (SEQ ID NO: 1) | 0 |
| Mycobacterium | LNVLRIVNEPTAAALAYGLD (SEQ ID NO: 2) | 2 |
| Maize | LNVMRIINEPTAAAIAYGLD (SEQ ID NO: 3) | 1 |
| Tobacco | LNVMRIINEPTAAAIAYGLD (SEQ ID NO: 3) | 1 |
| Tomato | LDVLRIINEPTAASLAYGFE (SEQ ID NO: 4) | 5 |
| Wheat | LRVLRIINEPTAAAIAYGLD (SEQ ID NO: 5) | 1 |

[1] amino acid positions 167-186
[2] amino acid positions 171-190

TABLE 2 second segment

| | | |
|---|---|---|
| Human[3] | NPDEAVAYGAAVQAAIL (SEQ ID NO: 6) | # differences human SEQ |
| Alfalfa[4] | NPDEAVAYGAAVQAAIL (SEQ ID NO: 6) | 0 |
| Mycobacterium | NPDEVVAVGAALQAGVL (SEQ ID NO: 7) | 5 |
| Maize | NPDEAVAYGAAVQAAIL (SEQ ID NO: 8) | 0 |
| Tobacco | NPDEAVAYGAAVQAAIL (SEQ ID NO: 8) | 0 |
| Tomato | NPDEVVALGASVQAGIL (SEQ ID NO: 9) | 4 |
| Wheat | NPDEAVAYGASVQAAIL (SEQ ID NO: 10) | 1 |

[3] amino acid positions 364-380
[4] amino acid positions 370-386

Additionally or alternatively the food product may comprise HSP or HSP-hydrolysate from another plant. In particular one or more HSPs or HSP-hydrolysates may be obtained from a plant selected from the group of cereals (for instance barley), soy, grasses (for instance oat), beet, potato, clover and water plants (for instance an alga). In particular, leaves of the plant may be used as source for one or more HSPs. Particularly suitable are beet tops, alfalfa leaves, barley leaves, oat leaves and potato tops. Although from achieving an intended medical effect, non-hydrolysed HSP may be particularly suitable, it is contemplated that in some embodiments, the presence of HSP-hydrolysate may be advantageous, in that it may be more resistant to detrimental effects of gastric juices or other food ingredients, than intact HSP, in particular if the HSP/HSP-hydrolysate is not present in a microparticle wherein it is protected by a protective encapsulating material or the like.

Further, it is contemplated that HSP and HSP-hydrolysate may display different pharmacokinetic and/or pharmocodynamic behaviour, for instance there may be difference in adsorption rate from the gastro-intestinal tract into the blood stream, a different distribution rate through the body, a different elimination rate, a difference intensity and or duration of its effectiveness at a specific concentration, e.g. as a result of a difference in interaction of the HSP respectively HSP-hydrolysate with HSP-sensitive receptors on cells.

Thus, by choosing for including HSP, HSP-hydrolysate, or both in a specific ratio, actual pharmacokinetic and/or pharmacodynamic behaviour may be modulated.

The HSP-hydrolysate may be obtained by chemical hydrolysis (in the presence of a strong acid, usually under heating or a strong base) or by enzymatic hydrolysis (using a proteolytic enzyme) based on technology known per se. Enzymatic hydrolysis is an effective alternative to chemical treatment. This process is mild in comparison to acid or alkali hydrolysis. Additionally, the inherent specificity of a specific proteolytic enzyme of choice can control the nature and extent of hydrolysis, and thus the functional properties of the end product.

The degree of hydrolysis may be chosen within wide limits. At least 10 wt. %, at least 25 wt. %, at least 50 wt. %, at least 80 wt. % or at least 90 wt. % (based on the sum of HSP-fragment and unhydrolysed HSP) of the HSP-hydrolysate may be formed by HSP fragments. Of the HSP-hydrolate 100 wt. % or less, 95 wt. % or less, at least 75 wt. % or less, 50 wt. % or less or 25 wt. % or less (based on the sum of HSP-fragments and unhydrolysed HSP) may be formed by HSP fragments.

The size of the fragments may be chosen within wide limits. Usually, in case a hydrolysate is present, at least 50 wt. %, in particular at least 75 wt. %, more in particular at least 90 wt. % (based on the sum of HSP-fragments and unhydrolysed HSP) of the hydrolysate is formed by peptides (including unhydrolysed HSP) having at least five amino acid residues. In a specific embodiment, at least 25 wt. %, in particular at least 50 wt. %, more in particular at least 75 wt. % (based on the sum of HSP-fragments and unhydrolysed HSP) of the hydrolysate is formed by peptides (including unhydrolysed HSP) having at least ten amino acid residues.

Usually, in case a hydrolysate is present, at least 10 wt. %, in particular at least 25 wt. %, more in particular at least 50 wt. % (based on the sum of HSP-fragments and unhydrolysed HSP) of the hydrolysate is formed by HSP fragments The food product may in particular comprise at least one HSP or hydrolysate thereof selected from the group of HSP40, HSP60, HSP70 and HSP 90, respectively hydrolysates of any of these HSPs.

The total concentration of heat shock protein plus hydrolysate thereof may be chosen within wide limits, usually in the range of 1 to 1 000 μg per 100 g product; preferred compositions depend on the type of product and its intended use. The total concentration of heat shock protein plus hydrolysate thereof per 100 g may be 10 μg or more, in particular 25 μg or more, more in 50 μg or more particular. The total concentration of heat shock protein plus hydrolysate thereof pre 100 g may be 1 000 μg or less, in particular 500 μg or less, more in particular 250 μg or less.

For a clinical food product the total concentration of heat shock protein plus hydrolysate thereof may advantageously be in the range of 25-250 μg/100 ml.

In a specific embodiment the food product is a clinical food product for infants, wherein the total concentration of heat shock protein plus hydrolysate thereof may in particular be chosen in the range of 50-100 μg per 100 ml.

In particular in a food product for oral consumption, such as a dairy product, a dairy substitute product, a fruit product or a soft drink, the concentration may be in the range of 50-250 μg/100 g product.

The HSP or HSP-hydrolysate may be present, dissolved in the product on a molecular scale or (homogeneously) dispersed in the product (e.g. in an emulsion), or be present in a particulate form.

In a specific embodiment, the food product contains microparticles comprising HSP or HSP-hydrolysate.

Microparticles are e.g. useful for realising a specific release pattern of the HSP or to protect the HSP or HSP-hydrolysate from an undesired interaction with the food product in which it is included, in the period between manufacture of the food product and administration to a subject. Microparticles have been defined and classified in various different ways depending on their specific structure, size, or composition, see e.g. Encyclopaedia of Controlled drug delivery Vol 2 M-Z Index, Chapter: Microencapsulation Wiley Interscience, starting at page 493, see in particular page 495 and 496.

As used herein, microparticles include micro- or nanoscale particles. Usually, at least the outer surface of the particles is composed of solid or semi-solid material. Typically, the average diameter of the microparticles given by the Fraunhofer theory in volume percent ranges from 10 nm to 1000 µm. The preferred average diameter depends on the intended use. For instance, in particular in case the microparticles are intended for parenteral administration, an average diameter of up to 10 µm may be desired.

It is envisaged that microparticles with an average diameter of less than 800 nm, in particular of 500 nm or less, are useful for intracellular purposes. For such purposes, the average diameter preferably is at least 20 nm or at least 30 nm.

In another embodiment, larger dimensions may be desirable, for instance a diameter in the range of 1-100 µm or 10-100 µm. It is envisaged that in particular for enteral feed tubing a relatively large diameter may be advantageous: in such embodiment factors such as unpleasant mouth feel due to a large particle size do not play a role, and a relatively large size may help to allow at least a substantial part of the HSP or HSP-hydrolysate to pass the stomach without being (further) degraded by the gastric fluid, which may be undesired at least in some embodiments.

In particular, the particle diameter as used herein is the diameter as determinable by a LST 230 Series Laser Diffraction Particle size analyzer (Beckman Coulter), making use of a UHMW-PE (0.02-0.04 µm) as a standard. Particle-size distributions are estimated from Fraunhofer diffraction data and given in volume (%).

If the particles are too small or non analyzable by light scattering because of their optical properties then scanning electron microscopy (SEM) or transmission electron microscopy (TEM) can be used.

The microparticle structure may be a substantially homogenous structure, including nano- and microspheres and the like. In an embodiment, the microparticles at least essentially consist of HSP or HSP-hydrolysate.

It is also possible to provide microparticles comprising a carrier or encapsulating material and the HSP or HSP-hydrolysate. Such carrier or encapsulating material may be mixed with the HSP or HSP-hydrolysate or surround the HSP or HSP-hydrolysate, such that particle with a nucleus comprising the HSP or HSP and a shell comprising the carrier or encapsulating material. Carrier materials and shell materials may herein be referred to under the generic name "encapsulating materials". The provision of a shell around a nucleus comprising the HSP or HSP-hydrolysate may be advantageous in that it may protect the HSP or HSP-hydrolysate, e.g. from interaction with the surroundings during storage (with other food ingredients, with water in the food product or with oxygen in the food product) or against the gastric juice (in case of an enteric shell). A carrier material mixed with the HSP may for instance be desired to accomplish a specific release profile of HSP or HSP-hydrolysate into the intestines or into the blood.

Suitable encapsulating materials are known in the art and may for instance be selected from (clinical) food grade biomolecules such as monosaccharides, disaccharides, oligosaccharides, digestible polysaccharides, non-digestible polysaccharides, proteins, fats and other lipids or (clinical) food grade synthetic molecules, in particular such molecules that can safely degrade or dissolve in the gastro-intestinal tract or in case of a parenteral nutritional product, that can release the HSP or hydrolysed HSP into the blood or into the target tissue (if any). Specific examples of encapsulating materials include gum acacia, maltodextrins, hydrophobically modified starch, alginate, carrageenan, pectin, guar gum, gum acacia, locust bean gum, gellan gum, agar, dextran, glucose, cyclodextrins, cellulose derivatives (such as carboxymethyl cellulose, methyl cellulose, ethyl cellulose), wax, paraffin, beeswax, diacyl glycerols, vegetable or animal oils/fats, whey proteins, soy proteins, sodium caseinate, gelatin, gluten, albumin, For example, HSP or HSP-hydrolysate may be encapsulated in a liposome, e.g. in a phospolipid liposome. It is contemplated that this may in particular be interesting, in case encapsulation is desired for a parenteral nutritional product.

In a specific embodiment, the shell may be an enteric coating, which is at least substantially resistant to the gastric juice, but which physically or chemically degrades in the intestines, to release the HSP or HSP-hydrolysates. Enteric coatings are known in the art, e.g. an enteric coating may comprise at least one component selected from the group consisting of cellulose acetate phthalate, cellulose acetate butylate phthalate, methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate and methyl methacrylate-methacrylic acid copolymers. Eudragit® is an example of a commercially available enteric encapsulating material.

In a specific embodiment, the HSP or HSP hydrolysate is encapsulated in food-grade material, that remains at least substantially undissolved and undegraded under gastric conditions, but that is dissolved or degraded in the intestine or affected in an other manner that causes the particles to disintegrate and release the HSP or HSP-hydrolysate.

Suitable methods of preparing microparticles are known in the art. The many available technologies for microencapsulation can be divided into two categories, one which uses a liquid as a suspending medium (complex coacervation, interfacial and in situ polymerization or solvent evaporation from emulsions) and one which uses a gas as a suspending medium into which a liquid phase is sprayed (spray-drying, spray-cooling or spray-chilling, fluidized-bed coating or coextrusion).

Well-known techniques are spray-cooling and spray-chilling. These techniques involve dispersing the water-soluble ingredient in a molten encapsulating material, such as fat or wax, and spraying this dispersion through heated nozzles into a chamber at ambient temperature (spray-cooling) or at refrigeration temperatures (spray-chilling). If the chamber is at room temperature, the encapsulation material usually has a melting point between 45 and 122° C. If the chamber is cooled, materials melting at 32-42° C. can be used.

A widely used microencapsulation technique in the food industry is spray drying. It is also applicable to encapsulating material that have no melting point or that have a melting point that is above the maximum temperature to which the HSP or hydrolysate should be exposed. The process is economical; flexible, in that it offers substantial variation in microencapsulation matrix; adaptable to commonly used processing equipment; and produces particles of good quality. Usually the HSP or HSP-hydrolysate is mixed with the encapsulating material in water or another suitable carrying liquid that can be removed from the (precursors of) the microparticles by drying. Examples of encapsulating materials that have been used in spray dry process (not necessarily with HSP or HSP-hydrolysate) include gum acacia, maltodextrins, hydrophobically modified starch, alginate, carboxymethylcellulose, guar gum, glucose (corn syrup), dextran, pectin, gellan gum, agar and proteins (whey proteins, soy proteins, sodium caseinate).

Methods of preparing microparticles by coacervation have been described in the prior art, also in relation to food technology, see e.g. WO 2007/026307 (using starch/starch hydrolysate).

Further, encapsulating methods that may be employed to provide microparticles for a food product according to the invention are, e.g., based on WO 2001/000233 (using alginate as encapsulating material), U.S. Pat. No. 4,232,047 (using e.g starch, protein (gelatin), flour, modified starch, gum, or mixtures thereof) or U.S. Pat. No. 4,230,687 (a controlled-release product prepared by dispersing an active agent in an encapsulant, such as modified starch, a gum, or a protein material such as gelatine or casein).

A food product (manufactured) in accordance with the invention may in particular be for the administration to a subject suffering from a chronic inflammatory disorder selected from the group of chronic arthritis, especially rheumatoid arthritis and atherosclerosis. In experiments with mice, it was found that chronic arthritis was suppressed in mice by treating them with alfalfa HSP70 (using a dosage of 250 µg administered four times in two weeks via intragastric gavage). From a comparison with experiments done by Wieten et al., who describe treatment of proteoglycan-induced arthritis using HSP70 from Mycobacterium (see Wieten et al. "IL-10 is critically involved in mycobacterial HSP70 induced suppression of proteoglycan-induced arthritis", PLoS ONE, January 2009, volume 4, issue 1, e34186), it was concluded that using alfalfa HSP70 in the treatment of chronic arthritis was about 30% more efficient than using HSP from mycobacterium for the same purpose.

The chronic arthritis may in particular be selected from primary forms of arthritis, such as from chronic forms of at least one disorder selected from the group of Osteoarthritis, Rheumatoid arthritis, Septic arthritis, Gout and pseudogout, Juvenile idiopathic arthritis, Still's disease, Ankylosing spondylitis.

In a specific embodiment, the food product is for the treatment of arthritis secondary to a disease selected from the group of Lupus erythematosus, Henoch-Schönlein purpura, Psoriatic arthritis, Reactive arthritis, Haemochromatosis, Hepatitis, Wegener's granulomatosis, Lyme disease, Familial Mediterranean fever, Hyperimmunoglobulinemia D with recurrent fever, TNF receptor associated periodic syndrome, Inflammatory bowel disease (Including Crohn's Disease and Ulcerative Colitis) or to a disease that can mimic arthritis, such as Hypertrophic osteoarthropathy Multiple myeloma, Osteoporosis or Fifth disease.

In a further embodiment, the food product is for administration to a subject suffering from a disorder selected from the group of chronic inflammatory bowel diseases, allergies (e.g. food or drug allergies), asthma, chronic obstructive pulmonary disease, scleroderma, psoriasis, atopic dermatitis, multiple sclerosis, cancers resulting from an inflammation, obesity associated with chronic inflammation, hypertension associated with chronic inflammation, stroke associated with chronic inflammation, diabetes associated with a chronic inflammation, Alzheimer associated with a chronic inflammation, and Parkinson's disease associated with a chronic inflammation. A disorder "associated with chronic inflammation" as used herein refers to a disorder that is caused at least in part by chronic inflammation.

The inflammatory bowel disease may in particular be selected from the group of Crohn's disease and ulcerative colitis. Other examples of inflammatory bowel disease that may be treated using a food product according to the invention include Collagenous colitis, Lymphocytic colitis, Ischaemic colitis, Diversion colitis, Behcet's syndrome, Infective colitis and Indeterminate colitis.

The cancer resulting from an inflammation may in particular be selected from the group of colon cancer, liver cancer, bladder cancer, and cervical cancer.

In addition to the HSP or HSP-hydrolysate, the food product (used) according to the invention may comprise one or more other active agents, e.g. a co-chaperone for the HSP or HSP-hydrolysate, but the food product may be free of such additional agents. It is contemplated that that the HSP or HSP-hydrolysate may be capable of interacting with an endogenous (formed in situ by the subject) co-chaperone or the like.

The food product may further comprise known ingredients for a specific food product, e.g. for a dairy product (milk or milk ingredients such as milk fat, milk protein), a dairy substitute product (a milk-substitute), a fruit product (processed fruit) or a soft drink (flavours, e.g. sugar, other sweeteners). Such food product may comprise additional food ingredients that are considered beneficial to a consumer's health, such as one or more ingredients selected from prebiotics, probiotics, and micronutrients, such as vitamins, minerals and the like. Suitable examples of additional ingredients are given below when discussing the enteral food.

An enteral food product may be based on a known formulation to which the HSP or HSP-hydrolysate are added, e.g. on a commercially available enteral food product. Usually the food ingredients, including the HSP or HSP hydrolysate, are dissolved or dispersed in water.

The enteral food product generally comprises at least one component selected from the group of amino acid sources, such as amino acids, oligopeptides, proteins; carbohydrate sources, such as monosaccharides, oligosaccharides, polysaccharides; and fatty acid sources, such as triglycerides and other fatty acid esters. In general it is preferred that an amino acid source, a carbohydrate source and a lipid source is present, in particular if it is desired to provide an at least substantially complete nutrition.

Examples of amino acid sources include soy protein, milk protein, hydrolysates of milk protein, hydrolysates of soy protein.

Examples of carbohydrate sources include glucose (e.g. corn syrup) and sucrose.

Examples of lipid sources include sources comprising triglycerides, such as vegetable oils, e.g. canola oil, fish oil, and medium chain triglycerides; and phospholipids.

Further, the enteral food product may comprise one or more micronutrients, in particular selected from the group of vitamins.

Examples of vitamins in particular include vitamin A, vitamin C, vitamin D (especially D3), vitamin E, pantothenate, niacinamide, riboflavin, folic acid, phytonadione, biotin, cyanocobalamin, pyridoxin, thiamin.

Examples of minerals, include sodium, potassium, magnesium, zinc, iron, copper, calcium, manganese, chromium, molybdenium, selenium, chloride, iodide, phosphor (phosphate).

Further, the enteral food product may comprise one ore more prebiotics, e.g. undigestible carbohydrates such as pectin, undigestible gum (such as gum arabic), fructooligosaccharide, gaslactoologisosaccharide, xylooligosaccharides.

Further, the enteral food product may comprise probiotics.

In addition one or more organic acids may be present (usually added in the form of a salt), such as citrate, acetate, gluconate.

In addition, one or more preserving agents may be present sorbate or the like.

Other suitable ingredients and suitable concentrations also may be based on what is known in the art from commercial products (e.g. ISOSOURCE FIN, Nesté) or published in writing, e.g. WO/2002/069964 of which the contents, in particular with respect to examples of suitable food ingredients and their concentrations, are incorporated herein by reference.

A parenteral nutritional composition is usually a solution, emulsion or dispersion of the food ingredients in water. It may in particular comprise one more food ingredients selected from the group of amino acid sources, carbohydrate sources, lipid sources, minerals and vitamins.

A parenteral nutrition may be based on commercially available or otherwise known formulations (to which HSP or HSP-hydrolysate is added). An example of a commercially available formulation is Intralipid.

As will be understood by the skilled person, the composition is formulated to be safe for administration into the bloodstream (physiological tonicity, physiological pH, non-immunogenic), and since the gastro-intestinal tract is bypassed, the food ingredients (with the exception of HSP/HSP-hydrolysate) are in general chosen such that they do not need degradation as would occur in the gastro-inestenal tract. Thus, the food ingredients (other than HSP/HSP-hydrolysate) will usually be low-molecular weight, in particular as a carbohydrate source a monosaccharide such as glucose is preferred, and as amino acid source amino acids are preferred. Thus, a parenteral nutritional product may for instance comprise HSP or HSP hydrolysate, and one or more of the following ingredients: electrolytes (NaCl, optionally composed of additional minerals, e.g. as mentioned for the enteral food product), amino acids, glucose, lipids, vitamins (e.g. as mentioned above for the enteral food product).

The invention further relates to a method for therapeutic treatment of a subject suffering from a chronic inflammatory disorder, in particular a disorder selected from chronic arthritis, especially rheumatoid arthritis, atherosclerosis, inflammatory bowel disease or another disorder as mentioned herein above respectively to a method for the prophylactic treatment of a subject in risk of developing any of these disorders.

The subject usually is a mammal, in particular a human, which may be an infant (<1 yr), an older child (1-12 yr), an adolescent (12-18 yr), or an adult in his early (19-39 yr), middle (40-65 yr) or late adulthood (>65 yr).

In a specific embodiment, the subject is a prematurely born neonate infant, in which case the food product typically is an enteral infant formulation. It is contemplated that in such embodiment the presence of HSP or HSP hydrolysate from alfalfa or another plant may help to prevent septic shock or may be used as part of a treatment of septic shock or may be used in the prevention or treatment of systemic inflammatory response syndrome. Such use may in particular be beneficial to prematurely born neonate infants, but other subjects, in particular other infants, may also benefit from such use.

Accordingly, in an embodiment, the invention is directed to the use of HSP or HSP hydrolysate from alfalfa or another plant (in the manufacture of a medicament, a nutritional product or a nutraceutical product) for the prevention or therapeutic treatment of systemic inflammatory response syndrome (SIRS). A nutritional product for use in the prevention or treatment of SIRS may in particular be a food product as described herein; the HSP or hydrolysate may in particular be HSP70 or a hydrolysate thereof Criteria for SIRS were established in 1992 as part of the American College of Chest Physicians/Society of Critical Care Medicine Consensus Conference. The conference concluded that the manifestations of SIRS (in humans) include, but are not limited to:

Body temperature less than 36° C. or greater than 38° C.

Heart rate greater than 90 beats per minute

Tachypnea (high respiratory rate), with greater than 20 breaths per minute; or, an arterial partial pressure of carbon dioxide less than 4.3 kPa (32 mmHg)

White blood cell count less than 4000 cells/mm$^3$ (4×109 cells/L) or greater than 12,000 cells/mm$^3$ (12×109 cells/L); or the presence of greater than 10% immature neutrophils (band forms)

SIRS can in particular be diagnosed when two or more of these criteria are present.

A method of treatment (or use) in accordance with the invention in general comprises the oral administration, parenteral administration or administration by tube feeding of the food. In the case of tube feeding, a tube for feeding is usually inserted into the stomach or intestines via the nose (nasogastric), the mouth, or via an incision in the abdomen into the stomach.

The dosage may be chosen within wide limits, depending on the intended use, the subject and the way of administration. As a rule of thumb a suitable average daily dosage is chosen in the range of 0.01 µg and 1 mg per kg bodyweight. Usually, the average daily dosage may be 0.1 µg per kg body weight or more, in particular 0.5 µg per kg body weight or more. Usually, the average daily dosage may be 100 µg per kg body weight or less, in particular 10 µg per kg body weight or less.

In terms of the dosage of heat shock protein plus hydrolysate thereof per administration (for bolus administration), this dosage usually is in the range of 10-1 000 µg, in particular 25-500 µg, more in particular 50-250 µg (for bolus administration).

The food product may, e.g. administered once a week; preferably the food product is administered at least once a day. The food product may be administered a plurality of time per day, e.g. ten times or less (especially in case the subject is an infant), six times or less, or three times or less. The clinical food product or other food product may be administered as a bolus. In particular, clinical food may be administered continuously.

The invention further relates to a method for preparing a food product according to the invention, comprising
  providing plant HSP, in particular HSP from alfalfa, isolated from the plant the HSP originates from, optionally hydrolysing the HSP or part thereof, and
  combining the HSP or HSP hydrolysate, with one or more further food ingredients, in particular one or more further food ingredients, as mentioned herein.

The plant HSP may be provided in a manner known per se. For instance, the plant HSP may be a plant HSP obtained by a method described in EP-A 1531160, of which the contents—in particular the claims and examples—are incorporated herein by reference.

In particular the HSP may be a plant HSP obtained by a method according European patent application with application number 09157774.2 (filed on 9 Apr. 2009, applicant Alfa Biogene International B.V.), of which the contents—in particular the examples, suitable process conditions and suitable materials for use in the method—are incorporated herein by reference.

More in particular the plant HSP may be obtained by a method for recovering HSP
  obtaining a liquid comprising the HSP from the plant;
  precipitating one or more components other than the HSP from the liquid;
  adding a fibrous filter aid and a mineral powder to the liquid; then
  subjecting the liquid comprising the HSP, precipitated component(s), the fibrous filter aid and the mineral powder to a first filtration step over a filter, thereby separating the precipitate, fibrous filter aid and mineral powder from the filtrate comprising the stress protein; thereafter
  subjecting the filtrate to a further filtration step; and thereafter
  purifying the HSP. The purified HSP may then be used in a method for preparing a food product according to the present invention.

In said method for recovering the HSP, the mineral powder preferably comprises at least one granular mineral, in particular at least one granular mineral selected from the group of diatomaceous earth and perlite.

In said method for recovering the HSP, the fibrous filter aid preferably comprises cellulose fibres.

In said method for recovering the HSP the fibrous filter aid preferably is a mixture of fibres having a different length, the mixture at least providing fibres with a length over the range of about 20 µm to about 130 µm.

In said method for recovering the HSP the further filtration step to which the filtrate is subjected may in particular be an depth filtration step.

In said method for recovering the HSP, after the further filtration step, a fraction comprising stress protein may be subjected to a fluid removal step thereby concentrating the stress protein in the fraction, preferably by reversed osmosis, ultrafiltration or nanofiltration, and/or to a salt removal step, preferably by dialysis.

The purification of HSP may in particular comprise chromatography. The chromatography preferably comprises a first strong anion exchange step, thereafter an affinity chromatography separation step, and thereafter a second strong anion exchange step. Suitable strong ion exchange separation materials are in particular those comprising trialkylammoniumalkyl functional groups, preferably trimethyl ammoniumethyl (TMAE) functional groups. The affinity chromatography materials may in particular be selected from chromatography materials for nucleotide-based affinity separation, preferably an adenosine based affinity separation, more preferably an ATP or ADP based affinity separation, even more preferably an affinity separation on ATP-agarose, ATP-sepharose, ATP-polyacrylamide, ATP-silica or ATP cellulose The median particle size of the exchange material used in the first anion exchange is preferably larger than the median particle size of the exchange material used in the second anion exchange.

If desired the HSP or part thereof may be hydrolysed, e.g. as described herein above.

The plant HSP or hydrolysate may be combined with the additional food ingredients in a process for preparing the food in a manner that is otherwise known per se, e.g. it may be combined with one or more other proteins and/or peptides (if present) which combination can then be further processed to product the food product of interest. Depending on the food product, it is also possible to added the HSP or hydrolysate to the food product already comprising the other ingredient(s).

What is claimed:

1. A method of prophylactically or therapeutically treating an individual with chronic arthritis comprising enterally administering to the individual a food product including a heat shock protein from alfalfa and/or a hydrolysate of a heat shock protein from alfalfa.

2. The method of claim 1 wherein the chronic arthritis is rheumatoid arthritis.

3. The method of claim 1 wherein the heat shock protein is HSP40, HSP60, HSP 70 or HSP 90 or a hydrolysate of HSP40, HSP60, HSP 70 or HSP 90.

4. The method of claim 1 wherein the total dosage of heat shock protein or hydrolysate thereof per dosage is in the range of 10-500 μg.

5. The method of claim 1 wherein the treatment comprises administering the food product by tube feeding.

6. The method of claim 1, wherein the food product comprises microparticles comprising the heat shock protein and/or hydrolysate thereof encapsulated in an enteric encapsulating material or other acid-stable encapsulating material.

7. The method of claim 1 wherein the food product is a dairy product, a substitute for a dairy product, a fruit product, a soft-drink or an infant formula.

8. The method of claim 1 wherein the total dosage of heat shock protein or hydrolysate thereof per dosage is in the range of 25-250 μg.

9. The method of claim 1 wherein the total dosage of heat shock protein or hydrolysate thereof per dosage is in the range of 50-200 μg.

10. The method of claim 1 wherein the heat shock protein is HSP 70.

11. The method of claim 1 wherein the heat shock protein is a hydrosylate of HSP 70.

12. The method of claim 1 wherein the heat shock protein is in the form of an isolate or fraction from alfalfa.

* * * * *

SEQUENCE LISTING

<160> NUMBER OF SEQ ID NOS: 10

<210> SEQ ID NO 1
<211> LENGTH: 20
<212> TYPE: PRT
<213> ORGANISM: Homo sapiens

<400> SEQUENCE: 1

Leu Asn Val Leu Arg Ile Ile Asn Glu Pro Thr Ala Ala Ala Ile Ala
1               5                   10                  15

Tyr Gly Leu Asp
            20

<210> SEQ ID NO 2
<211> LENGTH: 20
<212> TYPE: PRT
<213> ORGANISM: Mycobacterium sp.

<400> SEQUENCE: 2

Leu Asn Val Leu Arg Ile Val Asn Glu Pro Thr Ala Ala Ala Leu Ala
1               5                   10                  15

Tyr Gly Leu Asp
            20

<210> SEQ ID NO 3
<211> LENGTH: 20

```
<212> TYPE: PRT
<213> ORGANISM: Zea mays

<400> SEQUENCE: 3

Leu Asn Val Met Arg Ile Ile Asn Glu Pro Thr Ala Ala Ala Ile Ala
1               5                   10                  15

Tyr Gly Leu Asp
            20

<210> SEQ ID NO 4
<211> LENGTH: 20
<212> TYPE: PRT
<213> ORGANISM: solanum lycopersicum

<400> SEQUENCE: 4

Leu Asp Val Leu Arg Ile Ile Asn Glu Pro Thr Ala Ala Ser Leu Ala
1               5                   10                  15

Tyr Gly Phe Glu
            20

<210> SEQ ID NO 5
<211> LENGTH: 20
<212> TYPE: PRT
<213> ORGANISM: Triticum aestivum

<400> SEQUENCE: 5

Leu Arg Val Leu Arg Ile Ile Asn Glu Pro Thr Ala Ala Ala Ile Ala
1               5                   10                  15

Tyr Gly Leu Asp
            20

<210> SEQ ID NO 6
<211> LENGTH: 17
<212> TYPE: PRT
<213> ORGANISM: Homo sapiens

<400> SEQUENCE: 6

Asn Pro Asp Glu Ala Val Ala Tyr Gly Ala Ala Val Gln Ala Ala Ile
1               5                   10                  15

Leu

<210> SEQ ID NO 7
<211> LENGTH: 17
<212> TYPE: PRT
<213> ORGANISM: Mycobacterium sp.

<400> SEQUENCE: 7

Asn Pro Asp Glu Val Val Ala Val Gly Ala Ala Leu Gln Ala Gly Val
1               5                   10                  15

Leu

<210> SEQ ID NO 8
<211> LENGTH: 17
<212> TYPE: PRT
<213> ORGANISM: Zea mays

<400> SEQUENCE: 8

Asn Pro Asp Glu Ala Val Ala Tyr Gly Ala Ala Val Gln Ala Ala Ile
1               5                   10                  15

Leu
```

```
<210> SEQ ID NO 9
<211> LENGTH: 17
<212> TYPE: PRT
<213> ORGANISM: solanum lycopersicum

<400> SEQUENCE: 9

Asn Pro Asp Glu Val Val Ala Leu Gly Ala Ser Val Gln Ala Gly Ile
1               5                   10                  15

Leu

<210> SEQ ID NO 10
<211> LENGTH: 17
<212> TYPE: PRT
<213> ORGANISM: Triticum aestivum

<400> SEQUENCE: 10

Asn Pro Asp Glu Ala Val Ala Tyr Gly Ala Ser Val Gln Ala Ala Ile
1               5                   10                  15

Leu
```